United States Patent [19]

Domján nee Pinter et al.

[11] 4,399,306
[45] Aug. 16, 1983

[54] PROCESS FOR THE PREPARATION OF 2,6-DIALKYL-N-ALKOXYMETHYL-2-CHLORO-ACETANILIDES

[75] Inventors: Kornélia Domján née Pintér, Füzfógyártelep; György Huszák, Balatonfüzfo; Zoltán Kolonics, Balatonalmadi; László Lendvai; Jeno Pelyva, both of Füzfogyártelep; Endre Sümegi, Füzfogyartelep; Elemer Tömördi, Fertoszentmikles; Béla Györfi; László J. Szabó, both of Martonvásár; András Haas, Gyulafirátót; Miklós Kovacs, Veszprém; Tászló Kulcsár, Veszprem; Miklós Nadasy, Veszprem; Bálint Nagy, Veszprém; András Vass, Veszprém; Ervin Vértesi, Veszprém, all of Hungary

[73] Assignees: Nitrokémia Ipartelepek, Fuzfógyártelep; Nehezvegyipari Kutató Intézet, Veszprem; Mta Mezogazdásági Kutato Intezet, Martonvasar, all of Hungary

[21] Appl. No.: 104,918

[22] Filed: Dec. 18, 1979

[30] Foreign Application Priority Data

Apr. 24, 1979 [HU] Hungary .................. NI225

[51] Int. Cl.³ .................................. C07C 103/375
[52] U.S. Cl. .............................. 564/214; 564/143
[58] Field of Search ............ 260/562 R, 562 B; 564/143, 214

[56] References Cited

U.S. PATENT DOCUMENTS

| | | | |
|---|---|---|---|
| 2,863,752 | 12/1958 | Hamm et al. | 260/562 B X |
| 3,268,324 | 8/1966 | Hamm et al. | 260/562 B X |
| 3,347,858 | 10/1967 | Szarvasi et al. | 546/205 |
| 3,442,945 | 5/1969 | Olin | 260/562 B |
| 3,547,620 | 12/1970 | Olin | 260/562 B X |
| 3,630,716 | 12/1971 | Olin | 71/118 |
| 3,637,847 | 1/1972 | Olin | 260/562 R X |
| 3,875,228 | 4/1975 | Rathgeb et al. | 260/562 R |
| 3,937,730 | 2/1976 | Vogel et al. | 260/562 B |
| 4,070,179 | 1/1978 | Vogel et al. | 260/562 B X |
| 4,261,733 | 4/1981 | Chupp | 564/214 |
| 4,283,221 | 8/1981 | Vogel et al. | 564/214 X |
| 4,284,564 | 8/1981 | Alt et al. | 564/214 X |

FOREIGN PATENT DOCUMENTS

| | | | |
|---|---|---|---|
| 862713 | 6/1978 | Belgium | 564/143 |
| 1903198 | 8/1970 | Fed. Rep. of Germany | 562/214 |
| 2242420 | 3/1973 | Fed. Rep. of Germany | 260/562 B |
| 1543741 | 7/1973 | Fed. Rep. of Germany | 546/205 |
| 2405479 | 8/1974 | Fed. Rep. of Germany | 260/562 B |
| 2758418 | 7/1978 | Fed. Rep. of Germany | 562/214 |
| 1345667 | 1/1974 | United Kingdom | 562/214 |
| 1455474 | 11/1976 | United Kingdom | 562/214 |

OTHER PUBLICATIONS

Foreign Patent Journal, Belgium, Recueil Des Brevets d'Invention, Jan.–Feb. 1978, p. 377. Belgian Patent No. 862,713.
Derwent, Belgium Abstracts, 47734A/27 Belgian Patent No. 862,413.
Chemical Abstracts, "Patent Concordance", vol. 90, 1979, 24PC & 253 PC.

Primary Examiner—Thomas A. Waltz
Attorney, Agent, or Firm—Young & Thompson

[57] ABSTRACT

The invention relates to an improved method for the preparation of a 2',6'-dialkyl-N-alkoxymethyl-2-chloro-acetanilide compound of the general formula (I),

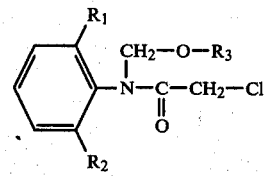

(I)

wherein
$R_1$, $R_2$ and $R_3$ are identical or different and stand for straight-chained or branched $C_{1-4}$ alkyl groups.

According to the invention a dialkyl aniline of the general formula (II),

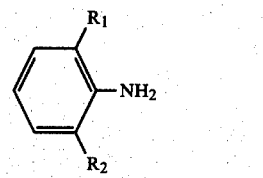

(II)

wherein $R_1$ and $R_2$ are as defined above, is treated with aqueous formaldehyde solution in an apolar solvent at a temperature of 30° to 80° C., the solution of the resulting oxymethyl derivative formed with said apolar solvent is separated from the aqueous formaldehyde solution at an elevated temperature and then dehydrated, the resulting azomethine derivative is reacted with chloroacetyl chloride in the same apolar solvent medium, the resulting chloromethyl compound is reacted with an alcohol of the general formula (V), $$R_3\text{-OH} \qquad (V)$$

wherein $R_3$ is as defined above, in an amount sufficient to bind the hydrochloric acid liberated in the reaction, the reaction mixture is admixed with water, and the organic phase containing the required end-product is separated and optionally processed.

9 Claims, No Drawings

PROCESS FOR THE PREPARATION OF 2,6-DIALKYL-N-ALKOXYMETHYL-2-CHLORO-ACETANILIDES

The invention relates to a novel process for the preparation of 2',6'-dialkyl-N-alkoxymethyl-2-chloroacetanilide compounds of the general formula (I),

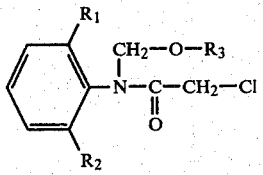

wherein
$R_1$, $R_2$ and $R_3$ are identical or different and stand for straight-chained or branched $C_{1-4}$ alkyl groups.

Owing to their excellent phytotoxic (primarily herbicidal) properties, these compounds can be applied to advantage in plant protection.

Several methods have been elaborated so far for the synthesis of the above compounds (see e.g. published German patent application No. 1,903,198, and U.S. Pat. Nos. 2,863,752, 3,547,620, 3,630,716, 3,875,228 and 3,637,847. All of these known methods utilize alkylanilines as starting substances and proceed through the steps shown in Scheme (A).

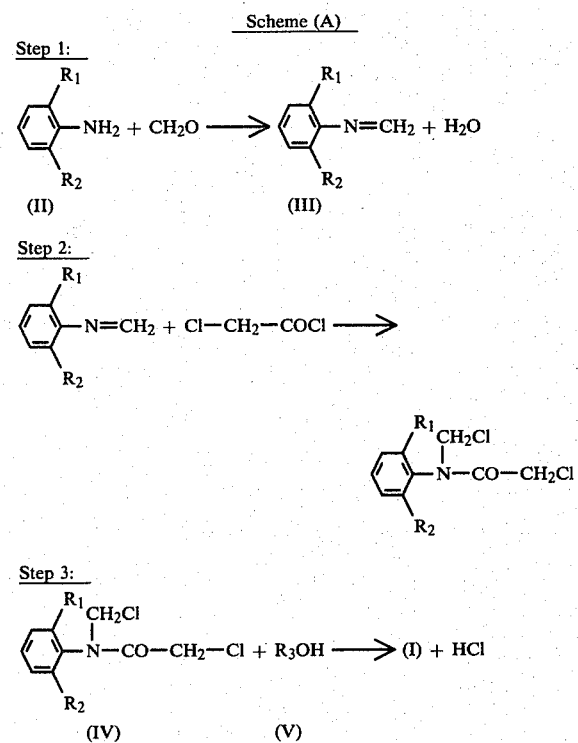

In the formulae $R_1$, $R_2$ and $R_3$ have the same meanings as defined above.

The various methods disclosed in the literature differ from each other in certain improvements relating to the complete process or to one or more of the reaction steps.

As shown in Scheme (A), the first step of the known methods is the reaction of an alkylaniline with formaldehyde, paraformaldehyde or trioxymethylene, leading to the formation of a Schiff base. The reaction is performed generally with an excess of aqueous formaldehyde solution also playing the role of solvent. In lieu of aqueous formaldehyde solution, paraformaldehyde or trioxymethylene, that is, oligomer forms of formaldehyde can be applied also in excess in the presence of an inert solvent. Water produced in the reaction is removed from the system. In the second step of the process the resulting Schiff base or azoalkenyl derivative is reacted with a haloacyl halide to form the respective N-(α-haloalkyl)-anilide. The reaction is terminated at about 100° C. after a reaction time of about 16 hours.

When reacting the Schiff base or the aromatic azomethine derivative with an acyl halide the individual components are generally added in stoichiometric amounts, in the presence of an inert organic medium, such as an aliphatic or aromatic hydrocarbon (e.g. n-heptane, benzene, toluene, xylene, etc.). The unreacted starting substances are removed by stripping or distillation. The reaction mixture is optionally washed with water, and the product is then separated by fractional distillation, selective extraction or crystallization.

The desired end-product is prepared e.g. according to the published German patent application No. 1,543,741 by reacting the N-(α-haloalkyl)-anilide intermediate as such, i.e. without any isolation or purification step, with a dry alcohol in the presence of an acid binding agent, and then separating the resulting product. In this alcoholysis, which is the third step of the synthesis shown in Scheme (A), alkali metal hydroxides or carbonates, tertiary amines or metal alcoholates can be applied as acid binding agents (see U.S. Pat. Nos. 3,442,945, 3,547,620 and 3,875,228).

The disadvantages connected to the various steps of the known syntheses are discussed in detail in the patent literature. Experimental results also indicate that the difficulties arising in the realization of the individual synthesis steps significantly affect the overall yield of the process, the purity grade of the end product and the economy of the synthesis.

In the Schiff base forming step the oligomeric formaldehyde derivative is applied in excess related to the starting alkylaniline, since after adding a stoichiometric amount, a significant part of dialkylaniline remains unreacted. The use of an excess of formaldehyde affects not only the economy of the process, but also makes the purification of the product difficult. Owing to its liability to sublimation, formaldehyde appears as impurity in the Schiff base and in the end-product even when these substances are purified by distillation or vacuum distillation. From practical aspects the use of aqueous formaldehyde is disadvantageous as well, since the removal of the introduced water by azeotropic distillation requires much time and energy. Paraformaldehyde should also be applied in excess in order to shift the equilibrium reaction to the desired direction, and the excess cannot be removed completely due to the liability of formaldehyde to sublimation.

The resulting Schiff base is reacted with a haloacyl halide generally at low temperatures, in order to prevent the reaction mixture from warming up excessively owing to the exothermic reaction. The completion of the reaction requires, however, a final treatment at 90° to 100° C. (see e.g. Example 2 of the U.S. Pat. No. 3,630,716). The resulting intermediate is generally separated by crystallization, or it is subjected directly to alcoholysis after cooling the reaction mixture. In this instance alcoholysis is started at a low temperature and terminated at elevated temperatures.

The alcoholysis itself may give rise to several additional side reactions leading to the formation of by-products, which appear as impurities in the desired product. Belgian Pat. No. 862,413 (published on June 28, 1978) states that according to the state of prior art the reaction cannot be performed with the desired result without acid binding agent. The majority of the compounds applied as acid binding agents react with the hydrogen halide liberated in the reaction to form a substance (e.g. ammonium chloride) which separates from the reaction medium as an insoluble precipitate. The removal of this precipitate from the mixture requires an additional step, e.g. extraction with water. When the reaction mixture is processed by distillation, acidic wastes are formed in large amounts, the disposal of which involves increasingly serious problems of environmental protection. It was also suggested to remove the hydrochloric acid formed in the reaction by vacuum distillation utilizing an excess of methanol, this operation, however, decreases the yield of the end-product owing to thermal decomposition. The cited Belgian patent suggests the use of several separation steps to remove hydrogen halides instead of binding them with a conventional acid binding agent. Accordingly, the reaction mixture is passed continuously through the individual stages. The first step runs with a conversion of about 92%, and a hydrochloric acid-chloroalkyl complex forms in addition to the desired end-product, the former remaining dissolved in the excess of methanol. This substance is distilled in a down film evaporator at a temperature of about 100° C. and under a pressure of 30 mmHg, and the complex obtained as intermediate is forwarded to the methanol recovering step. The unreacted starting substance, appearing in the overhead product of distillation, is reacted with additional amounts of alcohol in the second stage. This second stage is essentially a repetition of the process of the first stage. The purity of the resulting end-product is 95%, and its purity grade cannot be increased even by subjecting the product to repeated distillations. The alcoholysis described in the U.S. Pat. No. 3,547,620, performed in the absence of acid binding agent by reacting a 2-halo-2',6'-dialkyl-N-halomethyl-acetanilide with a substantial excess of an alcohol, proceeds with a conversion of only 83.7%. In this process about 7.5% of by-products are formed, and 5.5% of the starting substance remain unreacted despite the large excess of alcohol.

The known methods offer two ways to prepare pure 2-halo-2',6'-dialkyl-N-alkoxyalkyl-acetanilides. One of them is to perform the three synthesis steps without purifying the intermediates and purifying the end-product only, whereas according to the second method the individual intermediates are purified before the next reaction step. Both methods decrease the yield of the end-product, and, due to the high prices of the starting substances, also affect the economy of the complete process considerably. Besides the costs of the starting substances it should also be taken into account that the purification of the intermediates involves several technological difficulties, since these substances are sensitive to heat and liable to decomposition and polymerization. As appears from Belgian Pat. No. 862,413, the purity grade of the end-product cannot be increased over 95% even by subjecting the intermediates to purification.

The invention aims at the elimination of the disadvantages of the known processes. More particularly, the invention aims at the elaboration of an improved technology for the large-scale production of 2',6'-dialkyl-N-alkoxymethyl-2-chloro-acetanilides of good quality, according to which the purification of the intermediates can be omitted and the necessary investments can be decreased considerably.

Accordingly, the invention relates to an improved process for the preparation of 2',6'-dialkyl-N-alkoxymethyl-2-chloro-acetanilides of the general formula (I), wherein $R_1$, $R_2$ and $R_3$ are identical or different and stand for straight-chained or branched $C_{1-4}$ alkyl groups, by converting a dialkyl aniline into a Schiff base, and reacting the resulting Schiff base with a haloacyl halide and an alkanol. The process of the invention is performed so that a dialkyl aniline of the general formula (II),

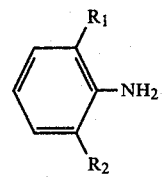

wherein $R_1$ and $R_2$ are as defined above, is treated with aqueous formaldehyde solution in an apolar solvent at a temperature of 30° to 80° C., the solution of the resulting oxymethyl derivative of the general formula (IIIA),

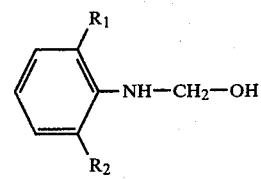

wherein $R_1$ and $R_2$ are as defined above, formed with said apolar solvent is separated from the aqueous formaldehyde solution at an elevated temperature and then dehydrated, the azomethine derivative of the general formula (III),

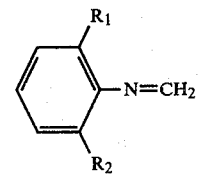

wherein $R_1$ and $R_2$ are as defined above, obtained in the dehydration step is reacted with chloroacetyl chloride in the same apolar solvent medium, the resulting chloromethyl derivative of the general formula (IV),

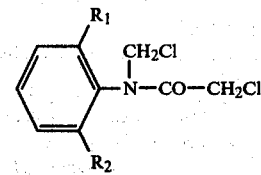

wherein $R_1$ and $R_2$ are as defined above, is reacted with an alcohol of the general formula (V),

wherein $R_3$ is as defined above, in an amount sufficient to bind the hydrochloric acid liberated in the reaction, the reaction mixture is admixed with water, the organic phase containing the required end-product is separated, and if desired, the end-product of the general formula (I) is removed from the organic phase by a method known per se.

In the first step of the synthesis the starting dialkyl aniline is admixed with an apolar solvent to obtain a mixture with a specific gravity of 0.90 to 0.92 at 20° C. As apolar solvent aromatic hydrocarbons forming azeotropic mixtures with water, preferably benzene or xylene, can be applied. The solution is then contacted with formaline. The aqueous formaline solution is separated at 60° to 90° C. from the organic phase containing the oxymethyl derivative of the general formula (IIIA). The organic phase containing the oxymethyl compound is dehydrated by subjecting it to azeotropic distillation at a temperature above 90° C. The resulting azomethine compound is then reacted with chloroacetyl chloride at 20° to 40° C. Alcoholysis is then performed in the same temperature range for about 5 to 8 hours. The alcohol is applied preferably in an at least fivefold excess related to the stoichiometric amount. After the termination of alcoholysis water is added to the reaction mixture, and the organic phase containing the end-product is washed acid-free.

The resulting product can be converted into plant protecting compositions either utilizing directly the organic solution obtained in the synthesis, or after isolating the end-product. The end-product is obtained according to the process of the invention in a purity grade of at least 96%, meeting the requirements of utilization as plant protecting agent.

Experimental results show that formaldehyde should be applied in excess in order to shift the equilibrium reaction of formaldehyde and the substituted aniline to the complete conversion of the aniline compound. Due to the presence of an excess of formaldehyde the known methods provide impure intermediates, which contain unreacted starting aniline compound and a substantial amount of formaldehyde as impurities. However, if the substituted aniline compound is reacted with aqueous formaldehyde solution according to the invention in a molar ratio of 1:1, and the aqueous formaldehyde solution is removed at a temperature of 80° to 140° C., complete conversion can be attained, and the amount of impurities appearing in the resulting oxymethyl intermediate is lower than 1%. The dehydration of the reaction mixture can be performed very easily by simple phase separation and subsequent azeotropic distillation. The aqueous formaldehyde solution can be separated very easily from the organic phase, since the aromatic solvent present provides a sufficient difference in specific gravity between the two phases.

The fact that the azomethine intermediate can be prepared according to the invention in high purity has further decisive and favourable effects on the subsequent steps of the synthesis. Thus e.g., the reactions with chloroacetyl chloride and alcohol can be performed at lower temperatures, furthermore no acid binding agent is required in the alcoholysis step, thus the problems connected with the use of acid binding agents (difficulties in the processing of the reaction mixture, lowering the purity grade and yield of the end-product, etc.) can be avoided. In the process of the invention one of the reagents, i.e. the alcohol itself, plays the role of acid binding agent, which, in contrast to the known processes, need not be removed continuously from the reaction mixture together with the liberated hydrochloric acid in order to attain complete reaction, allowing complete reaction even when it remains in the system during the whole process. The presence of uniform heat conditions in the synthesis is one of the preconditions of the simplification of technology and the elimination of by-product formation. Since the intermediates and the end-product of the synthesis are processed close to ambient temperature, a remarkable simplification of the technology can be achieved, avoiding thereby the disadvantage connected with the repeated heating and cooling operations. The solvent used in the synthesis may also be applied to advantage as azeotrope-forming, diluting and formulating agent, thus the reaction mixture obtained in the final step of the synthesis can be utilized directly for the preparation of plant protecting formulations. It is a further advantage of the homogeneous solvent medium applied in the process of the invention that it extracts the majority of organic components from the aqueous phase, thereby decreasing the amount of organic intermediates and end-product removed with the aqueous solution. This also simplifies the waste water treatment, enabling the organic substance content of the waste water to be reduced to minimum. The use of organic solvent does not increase the costs of the synthesis, since the solvent can be applied as formulating agent in the preparation of plant protecting compositions.

The main advantages of the process according to the invention related to the methods disclosed so far can be summarized as follows:

1. The new method offers a way for the continuous and economical large-scale production of important plant protecting agents in liquid phase.

2. The intermediates need not be purified separately, and the overall yield of the process and the purity grade of the end-product can be improved easily.

3. The amount of by-products appearing as impurities in the end-product can be reduced to the minimum; no foreign substance is to be introduced into the process; the energy balance is particularly favourable; the majority of the treatment steps with great energy demand (such as purification, isolation, crystallization, evaporation optionally in vacuo, cooling, etc.), applied between the individual reaction steps in the known methods, can be omitted; the process runs at an almost steady temperature.

4. Over the favourable energy balance it is also advantageous that the heat requirement of the end-product formation is minimum, there is no possibility of local overheating, and the formation of impurities or decomposition products upon heating can be avoided.

5. Waste waters formed in the process of the invention can be treated much more simply than those formed in the known processes, since, owing to the continuous presence of an organic phase, the concentration of organic impurities can be kept at minimum in the aqueous phase.

6. It is particularly remarkable that the preparation of the azomethine compound, i.e. the first intermediate, can be simplified considerably by applying aqueous formaldehyde solutions, without requiring the removal of large amounts of water by distillation.

7. The end-product can be obtained in a form directly applicable for plant protection purposes (i.e. as a solution formed with an organic solvent). This cannot be performed by the known methods, since, owing to the formation of by-products, isolation and purification steps had to be inserted between the individual synthesis steps, thus a formulation (a solution) applicable directly in plant protection could not be obtained.

The invention is elucidated in detail by the aid of the following non-limiting Examples.

EXAMPLE 1

Preparation of 2'-methyl-6'-ethyl-N-ethoxymethyl-2-chloro-acetanilide 135 kg (1 kmole) of 2-methyl-6-ethyl-aniline are introduced into a reactor equipped with an effective stirrer and a thermometer. 200 kg of xylene are added to the aniline compound, and the resulting solution is contacted countercurrently with a 40% aqueous formaldehyde solution containing 60 kg (2 kmoles) of formaldehyde at 70° to 80° C. At the same temperature the aqueous formaldehyde solution can be separated from the xylene solution containing the oxymethyl intermediate. The separated aqueous phase contains about 30 kg (1 kmole) of formaldehyde. This solution is recirculated into the synthesis. The resulting organic phase, containing 165 kg (1 kmole) of N-oxymethyl-2'-methyl-6'-ethyl-aniline, is dehydrated by subjecting it to azeotropic distillation at a temperature above 90° C. In this way the last traces of water can be removed.

The resulting xylene solution containing N-methylene-2'-methyl-6'-ethyl-aniline is introduced into a mixture of 120 kg (1.06 kmoles) of chloroacetyl chloride and 200 kg of xylene at 20° to 40° C. under continuous stirring. After about 15 minutes of stirring 250 kg (5.4 kmoles) of dry ethanol are introduced into the mixture at 20° to 40° C. The reaction mixture is stirred for 5 to 8 hours, whereupon alcoholysis proceeds. At the end of the reaction 600 kg of water are introduced into the mixture, and the phases are separated from each other. The upper (organic) phase is washed acid-free with about 1000 kg of water, and the xylene solution, containing about 250 kg of the desired end-product, is separated.

A sample of the resulting solution is evaporated, and the residue is subjected to gas chromatography. According to this analysis, the product contains 96% of 2'-methyl-6'-ethyl-N-ethoxymethyl-2-chloro-acetanilide, 2% of 2'-methyl-6'-ethyl-2-chloro-acetanilide and 2% of other unidentified by-products.

Similar results can be obtained when benzene is applied as solvent instead of xylene.

EXAMPLE 2

Preparation of 2',6'-dimethyl-N-methoxymethyl-2-chloro-acetanilide

One proceeds as described in Example 1 with the difference that 121 kg (1 kmole) of 2,6-dimethylaniline are applied as starting substance and 170 kg (5.3 kmoles) of methanol are utilized in the alcoholysis step. 220 kg of the desired product are obtained. Based on gas chromatographical analysis, the product contains 95% of 2',6'-dimethyl-N-methoxymethyl-2-chloro-acetanilide, 2.6% of 2',6'-dimethyl-2-chloro-acetanilide and 2.4% of other impurities.

EXAMPLE 3

Preparation of 2',6'-diethyl-N-methoxymethyl-2-chloro-acetanilide

One proceeds as described in Example 1 with the difference that 149 kg (1 kmole) of 2,6-diethylaniline are applied as starting substance and 170 kg (5.3 kmoles) of methanol are utilized in the alcoholysis step. 250 kg of the desired product are obtained with a purity grade of 96.2% (based on gas chromatography).

EXAMPLE 4

Preparation of 2',6'-diethyl-N-butoxymethyl-2-chloro-acetanilide

One proceeds as described in Example 1 with the difference that 149 kg (1 kmole) of 2,6-diethylaniline are applied as starting substance and 400 kg (5.5 kmoles) of n-butanol are utilized in the alcoholysis step. 290 kg of the desired product are obtained. Based on gas chromatographical analysis, the product contains 94.8% of 2',6'-diethyl-N-butoxymethyl-2-chloro-acetanilide, 2.8% of 2',6'-diethyl-2-chloro-acetanilide and 2.4% of unidentified impurities.

EXAMPLE 5

Preparation of 2'-methyl-6'-ethyl-N-methoxymethyl-2-chloro-acetanilide

One proceeds as described in Example 1 with the difference that 170 kg (5.3 kmoles) of methanol are applied in the alcoholysis step instead of 250 kg of dry ethanol. 235 kg of the desired product are obtained. Based on gas chromatographical analysis, the product contains 94.2% of 2'-methyl-6'-ethyl-N-methoxymethyl-2-chloro-acetanilide, 2.5% of 2'-methyl-6'-ethyl-2-chloro-acetanilide and 3.5% of unidentified other impurities.

EXAMPLE 6

Preparation of 2',6'-diethyl-N-ethoxymethyl-2-chloroacetanilide

One proceeds as described in Example 1 with the difference that 149 kg (1 kmole) of 2,6-diethylaniline are applied as starting substance. 265 kg of the desired product are obtained. Based on gas chromatographical analysis, the product contains 95.5% of 2',6'-diethyl-N-ethoxymethyl-2-chloro-acetanilide, 2.5% of 2',6'-diethyl-2-chloro-acetanilide and 2% of non-identified other impurities.

What we claim is:

1. In a process for the preparation of a 2',6'-dialkyl-N-alkoxymethyl-2-chloro-acetanilide compound of the general formula (I),

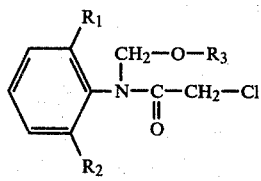 (I)

wherein $R_1$, $R_2$ and $R_3$ are identical or different and stand for straight-chained or branched $C_{1-4}$ alkyl groups, by converting a dialkyl aniline into a Schiff base, and reacting the resulting Schiff base with a haloacyl halide and an alkanol, and in which a dialkyl aniline of the general formula (II),

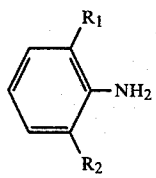 (II)

wherein $R_1$ and $R_2$ are as defined above, is treated with aqueous formaldehyde solution in an apolar solvent at a temperature of 30° to 80° C.; the improvement in which the solution of the resulting oxymethyl derivative of the general formula (IIIA),

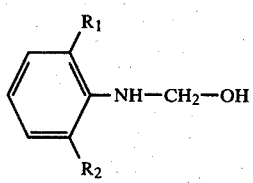 (IIIA)

wherein $R_1$ and $R_2$ are as defined above, formed with said apolar solvent is separated from the aqueous formaldehyde solution at an elevated temperature and then the separated apolar solvent containing the oxymethyl derivative of the general formula (IIIA) is dehydrated by azeotropic distillation at a temperature above 90° C. to remove the last traces of water, the azomethine derivative of the general formula (III),

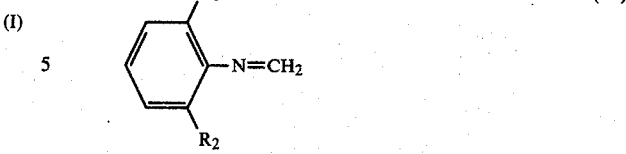 (III)

wherein $R_1$ and $R_2$ are as defined above, obtained in the dehydration step is reacted with chloroacetyl chloride in the same apolar solvent medium, the resulting chloromethyl derivative of the general formula (IV),

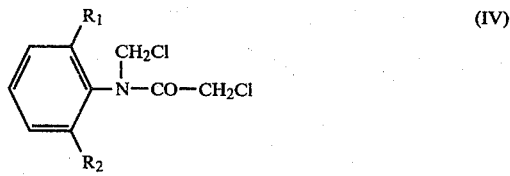 (IV)

wherein $R_1$ and $R_2$ are as defined above, is reacted with an alcohol of the general formula (V), $R_3\text{-OH}$ (V)

wherein $R_3$ is as defined above, in an amount sufficient to bind the hydrochloric acid liberated in the reaction, the reaction mixture is admixed with water, and the organic phase containing the required end-product is separated.

2. A process as claimed in claim 1, characterized in that a mixture of a specific gravity of 0.90 to 0.92 is formed from the starting dialkyl aniline and an apolar organic solvent.

3. A process as claimed in claim 1 or 2, characterized in that an aromatic hydrocarbon which forms an azeotropic mixture with water, the aromatic hydrocarbon being benzene or xylene, is applied as the apolar solvent.

4. A process as claimed in claim 1, characterized in that the aqueous formaldehyde solution is separated at 60° to 90° C. from the organic phase containing the dissolved oxymethyl derivative.

5. A process as claimed in claim 1, characterized in that the azomethine compound of the general formula (III), wherein $R_1$ and $R_2$ are as defined in claim 1, is reacted with chloroacetyl chloride at a temperature of 20° to 40° C.

6. A process as claimed in claim 1, characterized in that the alcoholysis is performed at a temperature of 20° to 40° C. for 5 to 8 hours.

7. A process as claimed in claim 1 or 6, characterized in that the alcohol is applied in an at least fivefold excess related to the stoichiometric amount.

8. A process as claimed in claim 1, characterized in that the organic phase containing the end-product is washed acid-free.

9. A process as claimed in claim 1, characterized in that said end product is separated from said organic phase.

* * * * *